United States Patent [19]

Colasante

[11] Patent Number: 5,070,223

[45] Date of Patent: Dec. 3, 1991

[54] MICROWAVE REHEATABLE CLOTHING AND TOYS

[76] Inventor: David A. Colasante, 38 Park St., Bldg. 18G, Florham Park, N.J. 07932-1744

[21] Appl. No.: 317,448

[22] Filed: Mar. 1, 1989

[51] Int. Cl.⁵ .............................................. H05B 6/80
[52] U.S. Cl. ...................... 219/10.55 M; 219/10.55 F; 219/10.55 R
[58] Field of Search .................. 219/10.55 F, 10.55 R, 219/10.55 M, 10.55 E, 211, 10.55 B; 128/379, 380, 381, 382

[56] References Cited

U.S. PATENT DOCUMENTS

| | | |
|---|---|---|
| 2,792,827 | 5/1957 | Gravin et al. |
| 3,292,628 | 12/1966 | Maxwell et al. |
| 3,569,666 | 3/1971 | Murphy et al. |
| 3,846,845 | 11/1974 | Englert et al. |
| 3,869,594 | 3/1975 | Shively ................................ 219/211 |
| 3,874,504 | 4/1975 | Verakas |
| 4,060,932 | 12/1977 | Leto et al. |
| 4,190,757 | 2/1980 | Turpin et al. ................. 219/10.55 E |
| 4,209,939 | 7/1980 | Pitalls |
| 4,316,070 | 2/1982 | Prosise et al. ................ 219/10.55 E |
| 4,362,917 | 12/1982 | Freedman et al. |
| 4,471,193 | 9/1984 | Walter .......................... 219/10.55 B |
| 4,486,640 | 12/1984 | Bowen et al. |
| 4,490,597 | 12/1984 | Mengel ......................... 219/10.55 E |
| 4,496,815 | 1/1985 | Jorgensen |
| 4,515,850 | 5/1985 | Ishino et al. |
| 4,518,651 | 5/1985 | Wolfe, Jr. |
| 4,535,482 | 8/1985 | Spector et al. |
| 4,538,630 | 9/1985 | Henderson ................... 219/10.55 A |
| 4,542,271 | 9/1985 | Tanonis et al. |
| 4,543,671 | 10/1985 | Monk |
| 4,568,298 | 2/1986 | Acree |
| 4,578,231 | 3/1986 | Molteni |
| 4,587,672 | 5/1986 | Madnick et al. |
| 4,640,838 | 2/1987 | Isakson et al. |
| 4,663,506 | 5/1987 | Bowen et al. |
| 4,689,460 | 8/1987 | Ishino et al. |
| 4,701,585 | 10/1987 | Stewart |
| 4,743,726 | 5/1988 | Hughes et al. ................ 219/10.55 F |
| 4,754,238 | 1/1988 | Schüller et al. |
| 4,795,649 | 1/1989 | Kearns et al. ................ 219/10.55 M |
| 4,849,593 | 7/1989 | Hughes et al. ................ 219/10.55 F |
| 4,866,231 | 9/1989 | Schneider .................... 219/10.55 A |
| 4,914,717 | 4/1990 | Gibbon ......................... 219/10.55 M |
| 4,931,608 | 6/1990 | Bills ............................... 219/10.55 F |

FOREIGN PATENT DOCUMENTS

| | | |
|---|---|---|
| 1221338 | 5/1987 | Canada |
| 0242952 | 10/1987 | European Pat. Off. |
| 0276654 | 8/1988 | European Pat. Off. |
| 0287323 | 10/1988 | European Pat. Off. |
| 0287324 | 10/1988 | European Pat. Off. |
| 62-298376 | 12/1987 | Japan |

Primary Examiner—Philip H. Leung
Attorney, Agent, or Firm—Mathews, Woodbridge & Collins

[57] ABSTRACT

Articles of apparel and a method of storing heat in same. The articles each consist of an object adapted to warm a carrier of the object, wherein the method comprises the steps of providing a reservoir within the object, the reservoir containing a supply consisting substantially of microwave absorbing compositions which repeatedly store heat, inserting the object with the reservoir in a field of microwave radiation, and activating the source for a predetermined period of time in order to heat the supply.

20 Claims, 2 Drawing Sheets

MICROWAVE REHEATABLE CLOTHING AND TOYS

BACKGROUND OF THE INVENTION

This invention relates generally to articles of apparel, and more particularly to methods of repeatedly storing heat in such articles of apparel.

For the purposes of this invention, the term "article of apparel" includes, but should not be considered as being limited to, clothing and other accessories which are worn or carried by a person. That is, the term "article of apparel" as is used herein denotes handwear, including gloves, mittens, muffs, hybrid glove-mitten designs, and other such means to be worn inside or as an accessory to handwear (e.g., by slipping such means inside of the handwear, by strapping such means on the handwear, or by attaching such means to the handwear such as by Velcro ®).

"Article of apparel" also refers to headwear (including earmuffs, headbands, hats, bandannas, yarmulkes, face masks, varied combinations of such types of headwear, and other such means to be worn inside or as an accessory to headwear); footwear (including slippers, shoes, boots, socks, insoles, arch supports, footwear inserts or other accessories to footwear); neckwear (including scarves, neckties, dickies, collars, or accessories to neckwear); various bodywear of a size that is capable of being fitted into a conventional microwave oven, which usually ranges in capacity of from 0.2 cubic feet to 5.0 cubic feet, including vests, jackets, undergarments, pocket warmers, and other such means to be worn inside or as an accessory to bodywear (e.g., by slipping such means inside of the bodywear, by strapping such means on the bodywear, or by attaching such means to the bodywear such as by Velcro ®).

It should also be noted that the term "article of apparel" herein encompasses toys (including dolls, carryable or huggable objects, renditions of food items, real or fictitious creatures, wearable toys and puppets); therapeutic appliances; and other objects which are preformed or compliant to body parts to which they would be applied (including pouches, bottles, bags, hot packs, compresses, wraps, masks, and other such means that are slipped inside of the therapeutic appliance, strapped on, buttoned on, or otherwise attached to the therapeutic appliance such as by Velcro ®).

Not only does an "article of apparel", as that term is used herein, include objects that are worn or carried by a person, but also other objects as exemplified above which are adapted to be worn or carried by, or applied to animals or other such living things.

2. Statement of the Prior Art

Since his beginnings man has been searching for methods and apparatus to keep warm. Warmth, provided by any suitable means, not only enables man to extend his range of activities to colder climates but also promotes a feeling of security. For example, a child can often be seen clutching a blanket or doll in order to be actually warmed by the blanket or doll and reassured by its presence.

The prior art is replete with means and methods of conserving the body's own warmth. Other means and methods have been developed to provide extracorporeal warming of various parts of the human anatomy, especially gloves and mittens for warming the hands of the wearer. Such known means and methods can be conveniently categorized under two typical approaches—electrical heating and chemical heating. For example, Maxwell et al. in U.S. Pat. No. 3,292,628 discloses an electric therapeutic glove comprised of an outside cover and inside liner between which is situated heating elements held in place by retaining screens, the heating elements being electrically energized as controlled by a thermostat.

In U.S. Pat. No. 3,569,666 issued to Murphy et al., a self-contained low voltage battery-operated glove is disclosed. The glove has a hand receiving portion, comprised of an outer covering and a complementary inner liner, and a wrist engaging portion in which a low voltage resistance heater is connected adjacent to the fingertip end portion of the inner palm side of the glove. The heater comprises a bare strip of electrical resistance material, sandwiched between a heat diffusing material, which is connected to the wrist portion of the glove on the back side thereof.

Monk, in U.S. Pat. No. 4,543,671, discloses a heated mitten which includes a main body for covering the hand and fingers of a wearer, and a thumb sheath together with an elasticated wrist band. The main body comprises a palm or front portion and a back or rear portion between which is formed a sealable compartment or pouch at the top of the mitten. The pouch includes an opening through which an electrical heating element is introduced, and is adapted to be moved to the front or back of the hand as necessary for warmth.

One obvious drawback to each of the above described electrically heated gloves or mittens is the necessity for a source of electrical power. Batteries often fail, and their subsequent replacement is often delayed because of lack of stores selling such batteries or because of a scarcity of batteries of a particularly required size. Another drawback is the repeated expense of the batteries and the lack of money at the time of need for such batteries. Furthermore, batteries perform suboptimally in cold weather which can impede the chemical reactions which produce the electrical outflow. Moreover, wear and tear on the gloves or mittens which incorporate such electrical heating elements increases the likelihood of shock or failure should the heating element become bare. It would, therefore, be desirable to provide an article of apparel, such as a glove, a mitten, or a cap, and method of heating same which does not require integral electrical heating means.

The other prior art approach—chemical heating—is also subject to many variations. For example, in U.S. Pat. No. 2,792,827 issued to Gravin et al., a heated glove is disclosed. The glove has a heating chamber formed as an auxiliary glove compartment which includes a waterproof and insulated main body with thumb and fingers superposing the main body, thumb and fingers of the hand of the glove. A heating tablet, powder or capsule is introduced within the heating chamber through its opened outer end together with a small quantity of water or other liquid, in order to develop heat through exothermic reaction. While any known heat generating chemicals, according to Gravin et al., may be used for the tablet, powder or capsule, the glove also utilizes a moisture absorbent layer on the interior of the heating chamber to prolong the chemical reaction between the moisture and such chemical composition.

Spector et al., in U.S. Pat. No. 4,535,482, discloses a heated glove having an inner layer of insulated material forming a sealable top pocket to hold a conventional fuel burning type hand warmer. Five ducts, each of which extend from the top pocket over a respective finger, provide warm air to the wearer's hand through a plurality of holes. The pocket is further provided with a top heat reflecting layer extending through the ducts, a zipper to close the pocket, and mesh screen placed below the zipper to allow ambient air to enter the pocket to supply oxygen to the hand warmer.

As is also disclosed in U.S. Pat. No. 4,587,672, issued to Madnick et al., a cold-weather hand covering can include a selectively shaped chemical heating element receiving chamber. Ten different embodiments of the cold-weather hand covering are shown, each including means for removably retaining the shaped element in its correspondingly shaped chamber.

While each of the above described chemical heating approaches eliminates the undesirable characteristic of having to be dependent upon a source of electricity as in the previously described electrical heating apparatus, such chemical heating apparatus nevertheless involves the usage of exhaustible and potentially undesirable components. It would, therefore, be more desirable to provide an article of apparel and method of heating same which permits the article to be repeatedly reheated without the presence of potentially undesirable and expendable chemical components.

The desirability to provide articles of apparel and method of heating same does not merely extend to article of apparel comprising pieces of clothing (e.g., glove, mittens or caps). Other articles, such as dolls, have been heated in the past in order to simulate the body temperature of an infant such that the carrier of the doll (most often a child) enjoys a greater sense of security and reality. For example, U.S. Pat. No. 4,060,932 issued to Leto et al. discloses a doll with an internal warming mechanism comprised of an internal vessel containing an exothermic salt and means to introduce water into the vessel to activate the salt and thereby release heat.

Pittala, in U.S. Pat. No. 4,209,939, also discloses a doll using circulating fluid to simulate body temperature. A skin structure in the doll, comprised of a spaced layer and stud passageway, permits fluid warmed by an electrically heated reservoir to be circulated throughout the doll. For the same reasons noted herein above with respect to the electrically and chemically heated gloves and mittens, however, a doll having some other means and method for warming the doll would be much more desirable.

SUMMARY OF THE INVENTION

Accordingly, it is a general object of the present invention to provide novel articles of apparel and a method of heating same. More particularly, it is an object of the present invention to provide articles of apparel which may be repeatedly reheated in order to warm the wearer or carrier of such articles.

Another object of the present invention is to provide articles of apparel which may be heated by a field of microwave radiation.

Still another object of the present invention is to provide cold weather garments which store heat produced by microwave radiation.

A further object of the present invention is to provide a mechanism for incorporation into dolls which simulates warm body temperatures through means which is activated by microwave radiation.

Briefly, the above and other objects according to the present invention are accomplished by a method of storing heat in an object adapted to warm a carrier of the object, wherein the method comprises the steps of providing reservoir means within the object, said reservoir means containing a supply of means for repeatedly storing heat, and inserting the object with said reservoir means in a field of microwave radiation for a predetermined period of time in order to heat said supply.

In accordance with one important aspect of the present invention, the reservoir means may be comprised of a flexible, substantially microwave-transparent material. The supply of means for repeatedly storing heat contained within the reservoir means, in accordance with a first embodiment of the present invention, is comprised of a substantial portion of a material such as water or preselected water-containing materials, such that the material will readily absorb microwave energy in order to produce heat energy.

Where flexibility is a desirable characteristic, the supply may consist of liquid or gels such as water only or a mixture of water and ethylene glycol or glycerine. On the other hand, where flexibility is not necessary, the supply is comprises of a microwave absorbing substance such as a hydrated crystal having a melting point below a predetermined maximum. "Composite materials", which include one component such as water to transduce microwave energy into heat energy and another component such as a petroleum derivative, a wax or crushed stone to store heat despite being substantially microwave transparent, may also be used. The "composite materials" would, thus, offer an advantage of storing heat in the other component at temperatures below the vaporization or melting points of the microwave transducing component, thereby protecting the reservoir means from overheating.

In accordance with another important aspect of the present invention, the source of microwave radiation is comprised of a microwave oven. Such ovens offer a source of microwave radiation having a standardized frequency. Furthermore, the variations in power output of such ovens are typically small so that their use with the reservoir means of the present invention is substantially safe when activated over the predetermined period of time.

In accordance with yet another important aspect of the present invention, the reservoir means may also include an inner bladder for containing the supply, and an outer bladder for protection from the occurrence a bursting inner bladder. The inner bladder may further comprise a conventional pressure releasing means to prevent such bursting. Alternatively, the microwave transducing component and heat absorbing component of the supply may themselves be solid and will, thus, together form the reservoir means.

Other objects, advantages, and novel features according to the present invention will become more apparent from the following detailed description thereof when considered in conjunction with the accompanying drawings wherein:

DETAILED DESCRIPTION OF THE INVENTION

Figure 1:
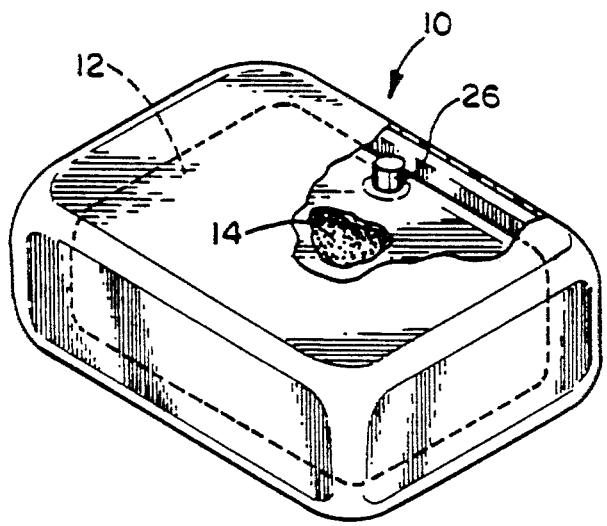
FIG. 1 illustrates a microwave renewable heat reservoir in accordance with a first embodiment of the present invention.

Referring now to the drawings, wherein like characters designate like or corresponding parts throughout the several views, there is shown in FIG. 1 one embodiment of a microwave renewable heat reservoir (MRHR) 10 in accordance with the present invention. The MRHR 10 is comprised generally of a substantially microwave-transparent bladder 12 containing a supply 14 of means for repeatedly storing heat.

The material from which the bladder 12 is formed should be flexible enough to be incorporated within articles of apparel as will be explained in greater detail herein below, and must be able to withstand the high temperatures reached by the contained means 14 during exposure to a field of microwave radiation. Examples of suitable such materials are films of polyesters or copolyesters, such as polyethylene terphthalate, polycarbonates and nylon, or polyvinyl chloride. An especially preferred film is a copolyester that allows for heat sealing of the bladder 12 since the MRHR 10 according to the present invention is not intended for replenishment of the supply 14 contained therein. Such an approach minimizes the chances of leaks from the bladder 12 and reduces the steps necessary for the use thereof.

The supply 14 is comprised substantially of microwave absorbing materials such as water or water-containing materials. As is known, "microwave absorbing materials" are also referred to variously as microwave lossy, microwave susceptible and microwave transducing materials, as opposed to "microwave transparent materials". The MRHR 10, therefore, comprises at least a first, microwave transducing component but it may also comprise a second, heat absorbing component.

In general, the microwave transducing components according to the present invention will absorb microwave energy as is typically produced within a conventional microwave oven, and will convert or transduce such absorbed microwave energy into heat energy. Suitable such microwave ovens emit microwave energy in the frequency range of from about 300 megahertz (MHz) to about 3000 MHz, preferably from about 2000 MHz to about 3000 MHz, and even more preferably at 2450 MHz, as well as harmonics of those frequencies which occur in the heating chambers of the microwave ovens. While conventional microwave ovens have power outputs in the range of from about 300 watts to about 1500 watts, it should be understood that the microwave transducing components according to the present invention are suitably adapted to transduce such absorbed microwave energy into heat energy at output powers in the range of from about 100 watts to about 2500 watts.

It is also desirable that such microwave transducing components be of low cost, lightweight, stable at a safe operating temperature, resistant to combustion, have low volatility, conform to any desired shape and consistency, be nontoxic, and possibly be edible. Since it is also desirable for the microwave transducing component to have the characteristic of a usable, relatively high heat capacity in order to reduce the need for the additional heat absorbing component, the microwave transducing component comprises preferably from about 0.1% to about 100% by weight of the MRHR 10, depending upon the efficiency of a selected microwave transducing component and its particular application. The efficiency, amount and concentration of the microwave transducing component will also determine the time which the MRHR 10 will require to become heated in a typical field of microwave radiation. This will, in turn, affect the uses and convenience of an article of apparel which incorporates an MRHR 10.

In those cases where the MRHR 10 is to be incorporated within an article of apparel requiring a substantial amount of flexibility, such as in a glove 18 (FIG. 2), the supply 14 may be comprised of a liquid such as water preferably mixed with a selected agent which would raise its boiling point. Where concern for toxicity is present, such as in those cases where the MRHR 10 is to be incorporated within an article of apparel to be worn or carried by a child, the selected agent could comprise glycerine mixed with water in substantially equal amounts of water and glycerine.

Figure 3:
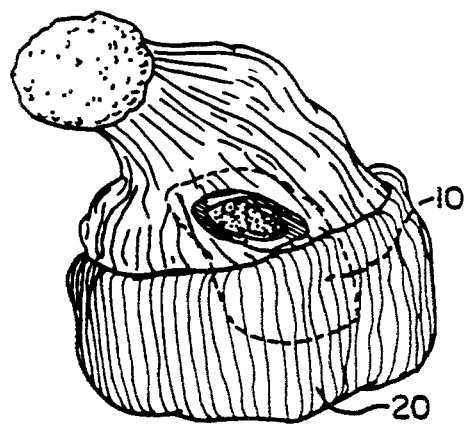
FIG. 3 illustrates another article of apparel which incorporates another microwave renewable heat reservoir in accordance with the present invention.

In those cases where the MRHR 10 is to be incorporated within an article of apparel which does not require flexibility, such as in a portable stadium cushion or in the lining of a cap 20 (FIG. 3), the supply 14 may be comprised of a selected microwave absorbing material, such as a hydrated crystal, having a melting point below a predetermined maximum. Examples of suitable such hydrated crystals are: aluminum nitrate—$Al(NO_3)_3 \cdot 9H_2O$; calcium acetate (also known as calcium acetate, dihydrate)— $Ca(C_2H_3O_2)_2 \cdot 2H_2O$; calcium chloride (also known as calcium chloride, hexahydrate)—$CaCl_2 \cdot 6H_2O$; calcium nitrate (also know as calcium nitrate, tetrahydrate)—$Ca(NO_3)_2 \cdot 4H_2O$; chromium nitrate (also known as chromium (III) nitrate)—$Cr(NO_3)_3 \cdot 9H_2O$; copper nitrate (also known as Copper (II) nitrate, hexahydrate)—$Cu(NO_3)_2 \cdot 6H_2O$; iron chloride (also know as iron (III) chloride, hexahydrate)—$FeCl_3 \cdot 6H_2O$; iron nitrate (also known as iron (III) nitrate)—$Fe(NO_3)_3 \cdot 6H_2O$; magnesium chlorate—$Mg(ClO_3)_2 \cdot 6H_2O$; potassium fluoride (also known as potassium fluoride, dihydrate)— $KFl \cdot 2H_2O$; potassium phosphate (also known as potassium subphosphate)—$K_2PO_3 \cdot 4H_2O$; sodium acetate—$Na_2H_3O_2 \cdot 3H_2O$; sodium carbonate (also known as washing soda)—$Na_2CO_3 \cdot 10H_2O$; sodium chlorite (also known as sodium chlorite, pentahydrate)—$NaOCl \cdot 5H_2O$; sodium phosphate (also known as monobasic sodium orthophosphate)—$NaH_2PO_4 \cdot 12H_2O$; and sodium chromate (also known as sodium chromate, decahydrate)—$Na_2CrO_4 \cdot 10H_2O$.

Because of the water contained in such hydrated crystals, the supply 14 made up of these crystals would gain heat upon exposure to the field of microwave radiation until such time that the crystals reached their melting point. Useful materials such as these crystals, in accordance with the present invention, have a melting point within the range of from 60°–180° F. After reaching the melting point of the crystals, the MRHR 10 further absorbs heat at substantially constant temperature until all of the crystals become melted. The temperature of the MRHR 10 then continues to rise to a predetermined maximum which may be selectively controlled by controlling the amount of time which the MRHR 10 is exposed to the field of microwave radiation.

In a cold operational environment, when incorporated within an article of apparel, the MRHR 10 having the supply 14 of hydrated crystals warms the wearer or carrier of the articles as follows. The liquified supply 14 while cooling to its "freezing" point gives off heat at an ever decreasing temperature. Thereafter, while the supply 14 continues to recrystallize, heat is given off at a substantially constant temperature until all of the crystals have been recrystallized. The process, as will be described in great detail herein below, is readily repeatable and thus provides a substantial source of heat for the wearer or carrier of the article of apparel.

While a desirable operating temperature of articles of apparel incorporating an MRHR 10 in accordance with the present invention is approximately 160° F., the actual temperature acquired by the MRHR 10 including its microwave transducing component may be much higher, thereby permitting a protective and insulating material to be interposed between the MRHR 10 and the wearer (or "carrier" or "body") to which it is applied. Such an insulating material is described more fully herein below with reference to FIG. 2. In such instances, the MRHR 10, and particularly its microwave transducing component, may reach temperatures as high as 750° F., though the temperature of the MRHR 10 in most applications preferably will not exceed 450° F., and even more preferably 200° F.

In addition to the examples of the supply 14 that are noted above, the microwave transducing component herein is most typically electrically conductive and/or magnetically permeable, especially if it is a metal. The microwave transducing components according to the present invention may also comprise, therefore, a ferromagnetic material, such as iron oxides and other metallic oxides, carbides, fire clay, ceramics (especially dielectric ceramics), silicon dioxide-containing ceramics, electrically conductive ceramics, magnetically permeable ceramics, and alkali titanates.

Alloys having the property of magnetic permeability, especially in combination with electrical conductivity, would also be appropriate. Examples of such alloys are Permalloy ®, and many alloys that contain aluminum, iron, cobalt, nickel, gadolinium, as well as gadolinium-terbium alloys, terbium-yttrium alloys, and dysprosium alloys. Materials displaying a Curie point would also be suitable to impart a desirable temperature-regulating feature to the MRHR 10. Other microwave transducing components which have been found suitable for purposes of the present invention are composites of electrically conductive materials with dielectric materials, as well as carbon.

More specifically, the MRHR 10 may comprise one or more of the above described microwave transducing materials, totalling from about 0.1% to about 100% by weight of the MRHR 10. Even more preferably, the microwave transducing components according to the present invention are suitably selected from the group consisting of: ferrite; soft ferrite; ferrite alloys such as nickel ferrite and magnesium ferrite; ferrites having the chemical formula of $MFe_2O_4$, where M is a metal of bivalence selected from the group consisting of calcium, barium, nickel, zinc, manganese, magnesium, and strontium; magnetite; lithium ferrite; carbonyl iron; iron; steel; iron oxide; ferric oxide; carbon (e.g., amorphous carbon, graphite in the form of particles, fibers or filaments, carbon chunks, charcoal, activated charcoal, carbon fibers, carbon filaments, carbon black, lamp black, furnace black, or channel black); polyesters, particularly alpha-beta unsaturated polyesters; aluminum, especially small particles or flakes thereof; gadolinium trichloride; boron trichloride; boron; barium titanate; strontium titanate; lead titanate; lead niobate; lead zirconate; nickel oxide; zinc oxide; silicon carbide; polyacetylene; cobalt; nickel; polycrystalline yttrium iron garnet; yttrium barium copper oxide; tin oxide; titanium dioxide; germanium dioxide; and butter fat as well as other such microwave transducing lipids especially those with unsaturated bonds. The above microwave transducing components may be of either natural or synthetic origin.

In accordance with another important aspect of the present invention, the heat absorbing component where incorporated in the MRHR 10, comprises from about 0% to about 99.9% by weight of the MRHR 10. While such heat absorbing components can be omitted from the MRHR 10, they will be preferably used with the microwave transducing components which have a relatively poor heat capacity. In order to effectively absorb and store thermal energy from the microwave transducing component, however, the heat absorbing (or "capacitive") component must be in contact with the microwave transducing component.

Such heat absorbing components may be solid, liquid or semi-solid depending upon the particular application. Especially preferable heat absorbing components comprise known phase change materials which absorb (or release) thermal energy at constant temperature during changes in phase. This can be effected through the mixing of one the components with the other in a solution, or a paste, or a paste that has hardened. Furthermore, one of the components may suitably serve as a coating or wrapping on the other component, or may also serve as a substrate with the other component dispersed throughout. Depending upon the application, either the microwave transducing component or the heat absorbing component will comprise a major portion of the supply 14.

Most desirable characteristics of the heat absorbing component of the MRHR 10 are its ability to contain large amounts of thermal energy at a given temperature, its resistance to combustion, its low volatility, its non-toxicity (possibly even edible), its stability at safe operating temperatures, its ability to mix or adhere to the microwave transducing component, its low cost, its low mass and compactness, and its ability to comply to any desired form factor in the article of apparel for which it is intended.

The heat absorbing material may also be relatively transparent to microwaves, although that is not necessarily a requirement. For example, it is not inconceivable that a single material such as water could serve as the microwave transducing component and the heat absorbing component, because of its substantial ability to transduce microwave energy into thermal energy and its substantial heat capacity. Certain other materials such as ceramics and lipids can also serve this dual role, as will other materials having not only a substantial ability to transduce microwave energy into thermal energy, but also a substantial heat capacity.

Specific materials which may be utilized as the heat absorbing component in accordance with the present invention, and which have suitably high heat capacities, include phase change materials (e.g., polyethylene glycols, waxes, microcrystalline waxes, paraffins and greases); ceramics; plastics, including thermoplastics and thermostable plastics; clay (both oil and water based); and certain metals or other solid materials which may be preshaped or powdered for compliance. Oils, including animal, vegetable and mineral oils, are also suitable for use as the heat absorbing component. Furthermore, certain known oils may be chemically modified such as by hydrogenation, to alter their melting points or heat capacity, thus enhancing their performance in the MRHR 10.

Suitable combinations of the above described microwave transducing components and heat absorbing components will not require the bladder 12 for their containment. For example, a ferrite or iron containing ceramic can be formed into tiles or beads which may be sewn into or otherwise attached to an article of apparel between layers of its material. Because such ceramics are dry solids, therefore, they require no bladder 12 and comprise a reservoir means by themselves in that form.

Certain known solid microwave transducing components may also be formed conventionally into fibers, coated with a phase change material such as polyethylene glycol to serve as the heat absorbing material, and woven into the material of the article of apparel. Thus, such a combination of the microwave transducing components with or without the heat absorbing component will also not require the bladder 12 for containment.

A reservoir means that is provided by the bladder 12 or a suitable carrier material will, nevertheless, offer advantages in certain cases when liquid, semi-solid, phase change (i.e., from solid to liquid and back), or dry components comprise the MRHR 10. In general, such carrier materials are adapted to hold together the microwave transducing and/or heat absorbing components. It is also desirable that the carrier materials be flexible, even in cold weather, stable at safe operating temperatures, nonvolatile, and resistant to combustion, melting and leakage when appropriate. Certain of the above-noted high temperature components of the MRHR 10 will further necessitate a carrier material having insulative characteristics.

In certain applications, the carrier material would not comprise a pouch such as the bladder 12, but would serve as a base upon which to mount the other microwave transducing and/or heat absorbing components of the MRHR 10. Therefore, in accordance with yet another important aspect of the present invention, the carrier material may comprise a fiber, film, fabric or sheet. The carrier materials may further be configured so as to channel the flow of thermal energy released from the MRHR 10 toward the user and reduce heat loss in other directions. Furthermore, the carrier material may suitably comprise a matrix network of spongy consistency, upon which the microwave transducing component (e.g., carbon) could adhere to and, thereby be held dispersed throughout a heat absorbing component (e.g., oil). Such a configuration will avoid any settling out of the microwave transducing component. A second carrier material in the form of the bladder 12 could also be utilized to contain all the above-described components to complete the MRHR 10.

Specific carrier materials, if used in the MRHR, may comprise one or combinations of more than one natural or synthetic materials selected from the group consisting of: cotton; cellulose; asbestos or other flame resistant fibers; jute; hemp; rubber; silicone rubber; nylon; polyester; aramid polypropylene; and other polyolefins.

It is clear from all of the above that the MRHR 10 may be fabricated into a wide variety of forms, each of which contains at least one microwave transducing component. However, the MRHR's 10 when incorporated into an article of apparel may be improved by the addition of other microwave transducing components, one or more heat absorbing components, or carrier components which would increase the heat capacity and efficiency of heat transfer to the user.

Figure 4:
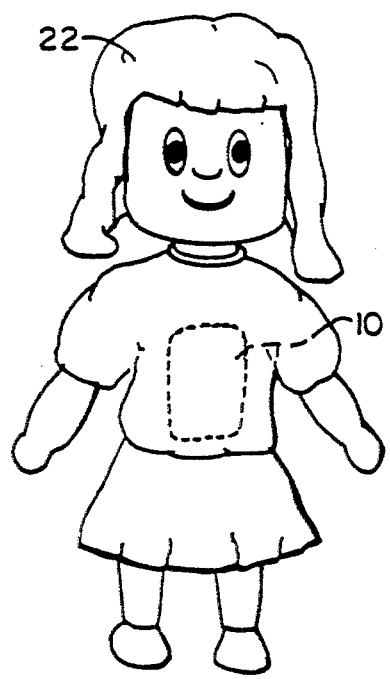
FIG. 4 illustrates a doll which incorporates the microwave renewable heat reservoir shown in FIG. 3.

As is readily apparent from FIG. 4, the MRHR 10 may be incorporated within an article of apparel used by a child, such as a doll 22. The MRHR 10 may be of the flexible type referred to herein above, or of a substantially rigid construction. In either case, the supply 14 contained within the MRHR 10 of the doll 22 should be non-toxic in order to avoid its accidental ingestion by the child. As such, the supply 14 shown in FIG. 4 may be comprised of the hydrated crystals referred to herein above, or may be comprised of a water/glycerine mixture, or any other non-toxic, microwave absorbing material including composites of such materials. Obviously, the materials comprising the doll 22 would of necessity be substantially microwave-transparent such that the MRHR 10 could be exposed to a source of microwave radiation in spite of its being sealed within the body of the doll 22.

Referring again to FIG. 1, the MRHR 10 in cases where there exists a substantial chance of bursting of the inner bladder 12 may be further comprised of an outer bladder 24 formed of a similar material as that of the inner bladder 12. Alternatively, or in addition to such outer bladder 24, the inner bladder 12 may be further comprised of a pressure releasing means 26 such as a conventional vent which is incorporated in many food products which are capable of being cooked in a microwave oven. The outer bladder 24 would thus provide additional protection against the occurrence of the bursting of the inner bladder 12, while the pressure releasing means 26 would substantially preclude the occurrence of such bursting.

Figure 2:
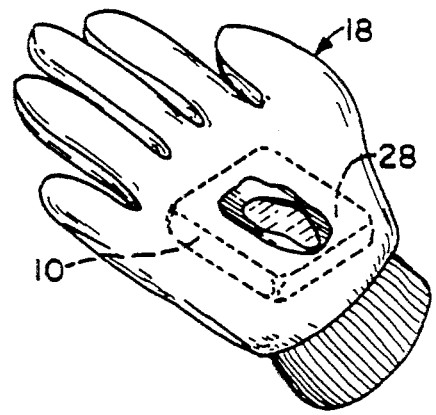
FIG. 2 illustrates an article of apparel which incorporates the microwave renewable heat reservoir shown in FIG. 1.

In cases where the MRHR 10 is incorporated within an article of apparel which is intended to be worn or carried in intimate contact with portions of the anatomy of the wearer or carrier, such as in the glove 18 shown in FIG. 2, the MRHR 10 may be further comprised of an insulative outer surface 28 in order that a maximum amount of heat can be radiated inward toward the wearer or carrier.

As noted above, when the microwave transducing component alone, or the microwave transducing component and heat absorbing component together is solid, a carrier material is not required. Such components may be suitably formed into preshaped or flexible (e.g., plastics) plates, sheets, foils, flakes, or tiles, or beads, particles or grains which could be incorporated into the article of apparel. Such solids may be suitably formed into filaments, fibers, threads or whiskers which may be knitted or made into woven, or nonwoven fabrics or mesh of one or more piles. As such, additional heat capacity may be added to the resulting MRHR 10 by coating the solids with heat absorbing components such as a phase change material (e.g., polyethylene glycol).

When the microwave transducing components, or the combination of microwave transducing components and heat absorbing components are a liquid, powder or semisolid form, such as gels, colloids, pastes and creams, a leakproof reservoir means such as the bladder 12 will be required. Such reservoir means will also be required in cases where phase change materials are employed and those materials will liquify in the vicinity of the operating temperature of the MRHR 10.

Figure 5:
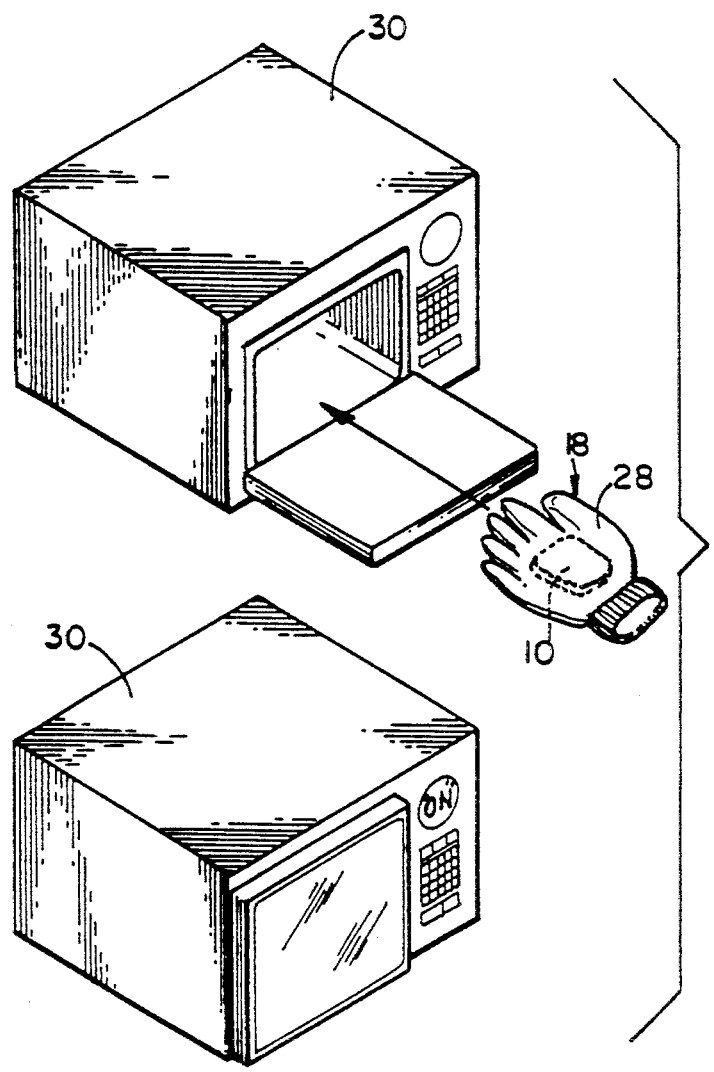
FIG. 5 a method of storing heat in the microwave renewable heat reservoir.

Referring now to FIG. 5, a method of storing heat in the MRHR 10 will now be explained. Having provided the reservoir means as described herein above with reference to the MRHR 10, the particular article of apparel within which the MRHR 10 is incorporated is inserted within a field or source 30 of microwave radiation, such as a conventional microwave oven. Since such ovens have become more and more readily available, and since the range of powers at which they operate are constrained about a predictably small wattage range, the article having the MRHR 10 can be carefully heated over a predetermined period of time without undue risks of overheating or bursting. Furthermore, since the MRHR 10 according to the present invention is adapted to be sealed with the article, there is not need to remove the MRHR 10 before exposing it and the article to the source 30 of microwave radiation as long as the article itself is substantially microwave-transparent. As most articles of apparel, particularly clothing, are made of natural or synthetic polymer fibers, the desirable microwave-transparency is readily achievable. After having inserted the article and the MRHR 10 within the source 30, the source 30 is activated for the predetermined period of time, removed from the source 30, and worn or carried to provide heat to the user.

Figure 6:
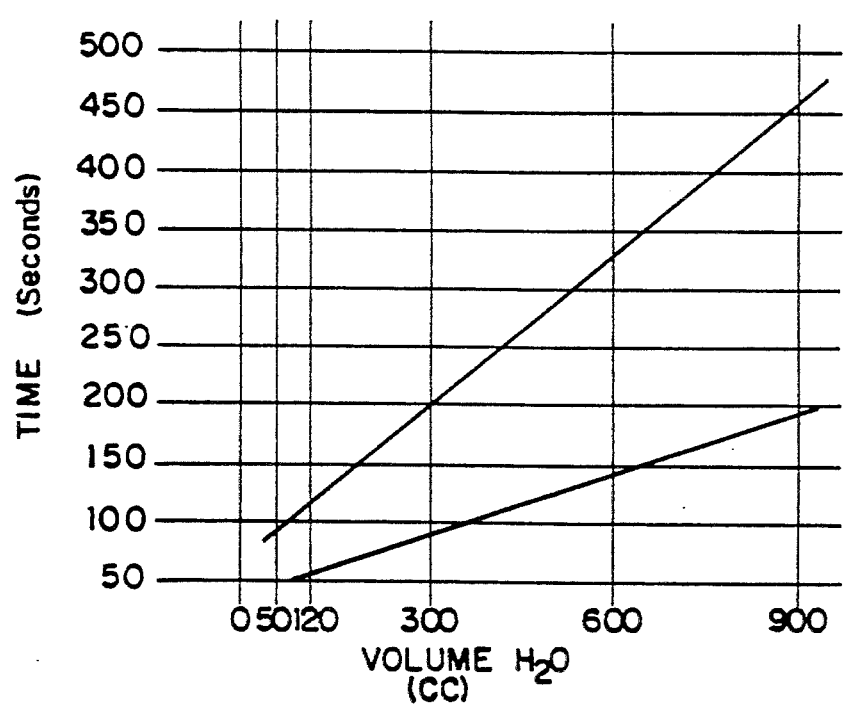
FIG. 6 illustrates an exemplary time-volume relationship for carrying out the method shown in FIG. 5.

As shown in FIG. 6, the predetermined time for activation is dependent upon the volume of the supply 14 contained within the MRHR 10. Specifically, FIG. 6 illustrates the time to heat a given amount of water from about room temperature to 130° F. and 200° F. respectively. The microwave oven used for such tests had a rated power of 650 watts, although greater or lesser powered microwave ovens (e.g., from 100 watts to 2500 watts) would have a slight effect on such time. For example, tests in microwave ovens ranging in power from 400 watts to 900 watts have demonstrated that a given volume of water heated over the same amount of time varied in a final temperature of only 12° F. Generally, however, increasing the volume of the supply 14 to be heated by five to fifteen times merely increases the times to achieve a given temperature goal of approximately five and fifteen times respectively.

Other safety means may be incorporated within the MRHR 10. For example, cellulose, starch, proteins that are thickeners, and fibers have been used to form a paste of the otherwise liquid components of the MRHR 10 in order to reduce risks of burning by hot liquids escaping from the MRHR 10. Other pastes, powders, or waxes which are not liquid at the safe operating temperatures of the MRHR 10 also reduce such burn hazards. A highly absorbent, insulating material to catch escaping liquids, a material having a strong, readily identifiable odor when heated by the escaping hot liquids, or a material adapted to be repellant to liquids (e.g., such as by application of ScotchGuard ®) may also be used to provide a certain measure of safety. Likewise, the MRHR 10 may include a temperature indicator which changes color or shape for indication of desirable versus undesirable temperature conditions.

Obviously, many modifications and variations of the present invention are possible in light of the above teachings. For example, the garments which incorporate an MRHR may include all forms of handwear, headwear, footwear, and other clothing. It is, therefore, to be understood that within the scope of the appended claims, the invention may be practiced otherwise than as specifically described herein.

What I claim is:

1. A toy comprising:
   a doll; and
   an enclosed reservoir within the doll, the reservoir containing a microwave absorbing composition including at least one material selected from the group consisting of electrically conductive materials, magnetically permeable materials, materials having a Curie point, composites of electrically conductive materials with dielectric materials, and carbon, combined with at least one phase changing material selected from the group consisting of crystals and polymers whereby said composition heats to a predetermined temperature when the doll is placed in an operating microwave oven.

2. The toy as recited in claim 1 wherein the reservoir comprises a flexible, substantially microwave transparent.

3. The toy as recited in claim 1 further comprising a reservoir comprising a carrier means for carrying the microwave absorbing composition.

4. The toy as recited in claim 1 wherein the at least one phase changing material is selected from the group consisting of sodium acetate and polyethylene glycol.

5. The toy according to claim 1, wherein said at least one material comprises electrically conductive materials selected from the group consisting of iron oxides and other metallic oxides, carbides, fire clay, ceramics, silicon dioxide-containing ceramics, magnetically permeable ceramics, and alkali titanates.

6. The toy according to claim 1, wherein said at least one material comprises electrically conductive and magnetically permeable materials selected from the group consisting of alloys that contain aluminum, iron, cobalt, nickel, gadolinium, gadolinium-terbium alloys, terbium-yttrium alloys, and dysprosium alloys.

7. The toy according to claim 1, wherein said at least one material comprises materials selected from the group consisting of ferrite, soft ferrite, ferrite alloys including nickel ferrite and magnesium ferrite, magnetite, lithium ferrite, carbonyl iron, iron, steel, iron oxide, ferric oxide, carbons including amorphous carbon, graphite in the form of particles, fibers or filaments, carbon chunks, charcoal, activated charcoal, carbon fibers, carbon filaments, carbon black, lamp black, furnace black, and channel black, polyesters including alpha-beta unsaturated polyesters, aluminum including small particles or flakes thereof, gadolinium trichloride, boron trichloride, boron, barium titanate, strontium titanate, lead titanate, lead niobate, lead zirconate, nickel oxide, zinc oxide, silicon carbide, polyacetylene, cobalt, nickel, polycrystalline yttrium iron garnet, yttrium barium copper oxide, tin oxide, titanium dioxide, germanium dioxide, butter fat and microwave transducing lipids including those with unsaturated bonds.

8. A method comprising:
   placing an article selected from the group consisting of clothing and toys, in a microwave heating apparatus, said article comprising an enclosed reservoir, said reservoir containing a microwave absorbing composition including at least one material selected from the group consisting of electrically conductive materials, magnetically permeable materials, materials having a Curie point, composites of electrically conductive materials with dielectric materials, and carbon, combined with at least one phase changing material selected from the group consisting of crystals and polymers; and heating said article with microwave radiation generated by said microwave apparatus, whereby said composition heats to a predetermined temperature.

9. The method as recited in claim 8 further comprising the step of reheating the article with microwave radiation.

10. An article comprising:
at least one item of clothing selected from the group consisting of a glove, a mitten, an ear muff, a hat, a slipper, a shoe, a boot, and a sock;
a reservoir means within the clothing, the reservoir containing a microwave adsorbing composition including at least one material selected from the group consisting of electrically conductive materials, magnetically permeable materials, materials having a Curie point, composites of electrically conductive materials with dielectric materials, and carbon, combined with at least one phase changing material selected from the group consisting of crystals and polymers.

11. The apparatus as recited in claim 10 wherein the reservoir means further comprises a bladder, the bladder containing the microwave absorbing composition.

12. The apparatus as recited in claim 10 wherein the reservoir means further comprises a carrier, the carrier containing the microwave adsorbing composition.

13. The apparatus as recited in claim 10 wherein said at least one phase changing material is polyethylene glycol.

14. The article as recited in claim 10 wherein the item of clothing is selected from at least one glove and at least one mitten.

15. The article as recited in claim 10 wherein the item of clothing is a hat.

16. The article as recited in claim 10 wherein the item of clothing is at least one ear muff.

17. The article as recited in claim 10 wherein the clothing is selected from at least one slipper and at least one sock.

18. The article according to claim 10, wherein said at least one material comprises electrically conductive materials selected from the group consisting of iron oxides and other metallic oxides, carbides, fire clay, ceramics, silicon dioxide-containing ceramics, magnetically permeable ceramics, and alkali titanates.

19. The article according to claim 10, wherein said at least one material comprises electrically conductive and magnetically permeable materials selected from the group consisting of alloys that contain aluminum, iron, cobalt, nickel, gadolinium, gadolinium-terbium alloys, terbium-yttrium alloys, and dysprosium alloys.

20. The article according to claim 10, wherein said at least one material comprises materials selected from the group consisting of ferrite, soft ferritte, ferrite alloys including nickel ferite and magnesium ferrite, magnetite, lithium ferrite, carbonyl iron, iron, steel, iron oxide, ferric oxide, carbons including amorphous carbon, graphite in the form of particles, fibers or filaments, carbon chunks, charcoal, activated charcoal, carbon fibers, carbon filaments, carbon black, lamp black, furnace black, and channel black, polyesters including alpha-beta unsaturated polyesters, aluminum including small particles or flakes thereof, gadolinium trichloride, boron trichloride, boron, barium titanate, strontium titanate, lead titanate, lead niobate, lead zirconate, nickel oxide, zinc oxide, silicon carbide polyacetylene, cobalt, nickel, polycrystalline yttrium iron garnet, yttrium barium copper oxide, tin oxide, titanium dioxide, germanium dioxide, butter fat and microwave transducing lipids including those which unsaturated bonds.

* * * * *